United States Patent [19]

Diamandis et al.

[11] Patent Number: 5,089,423
[45] Date of Patent: Feb. 18, 1992

[54] IMMUNOASSAY METHODS AND REAGENTS AND METHODS FOR PRODUCING THE LATTER

[75] Inventors: Eleftherios P. Diamandis; J. Alexander Lowden, both of Toronto, Canada

[73] Assignee: CyberFluor Inc., Toronto, Canada

[21] Appl. No.: 190,926

[22] Filed: May 6, 1988

[30] Foreign Application Priority Data

May 6, 1987 [CA] Canada ................................. 536511

[51] Int. Cl.⁵ ............................................. G01N 33/543
[52] U.S. Cl. ................................. 436/518; 436/546; 436/800; 436/817
[58] Field of Search ............... 436/518, 56, 546, 172, 436/800, 817; 424/7.1; 530/389, 390, 807

[56] References Cited

U.S. PATENT DOCUMENTS

| | | | |
|---|---|---|---|
| 4,434,150 | 2/1984 | Azad et al. | 436/518 |
| 4,486,530 | 12/1984 | David et al. | 435/7 |
| 4,637,988 | 6/1987 | Hinshaw et al. | |
| 4,772,563 | 9/1988 | Evangelista et al. | |
| 4,803,170 | 12/1989 | Stanton et al. | 436/518 |
| 4,837,169 | 6/1989 | Toner | 424/7.1 |

OTHER PUBLICATIONS

Smith, Ann. Clin. Biochem., vol. 18, pp. 253-274, 1981.
Oellerich, M., J. Clin. Chem Clin. Biochem., vol. 22 (12), pp. 895-904 (1984).
Uotila et al., Chemical Abstracts; vol. 94;190054g (1981).
The Wako Pure Chemical Industries, Ltd., Chemical Abstracts, vol. 101:104944f (1984)

*Primary Examiner*—Mary E. Ceperley
*Attorney, Agent, or Firm*—Banner, Birch, McKie & Beckett

[57] ABSTRACT

Immunoassay and methods for using fluorescent chelates of lanthanide metal ions in conjunction with immunoreactive bodies to permit fluorescent assay in liquid or dry samples. The assay reagent comprises a residue of an immunoreactive body linked to a residue of a protein or polypeptide. The protein or polypeptide is labeled by substitution with a ligand forming a fluorescent chelate with lanthanide metal ion such as europium. The reagent when used in an immunoassay, binds to the immobilized immunoreactive body and excess is washed away. The sample can be dried for later analysis by a suitable fluorometer.

11 Claims, 8 Drawing Sheets

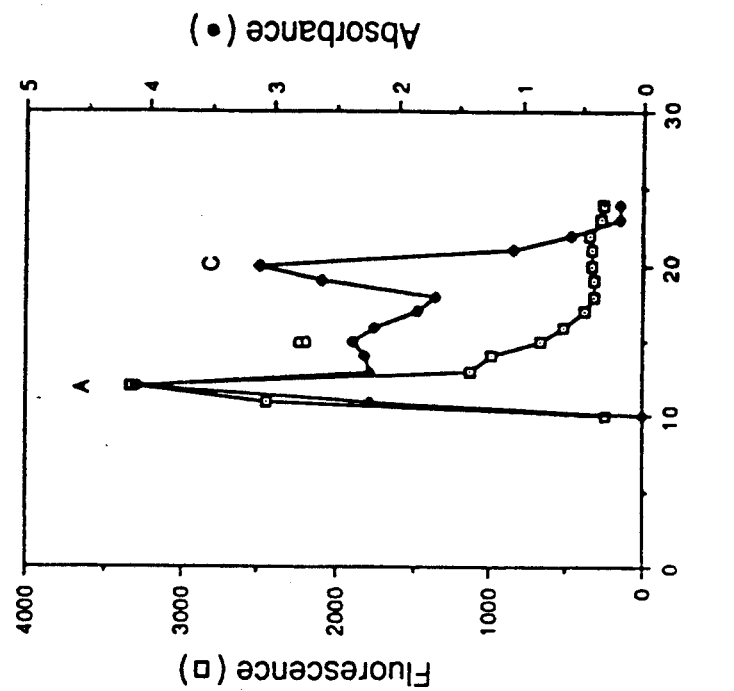
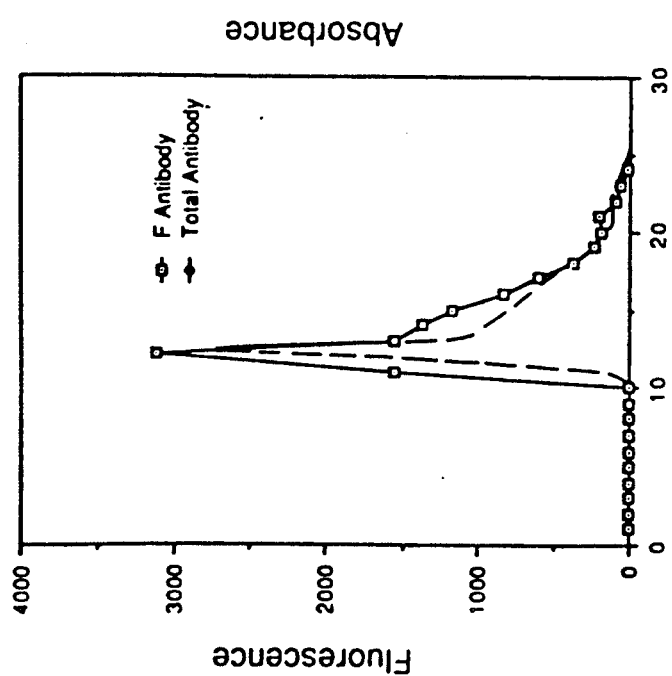
FIG. 2b
FIG. 2a

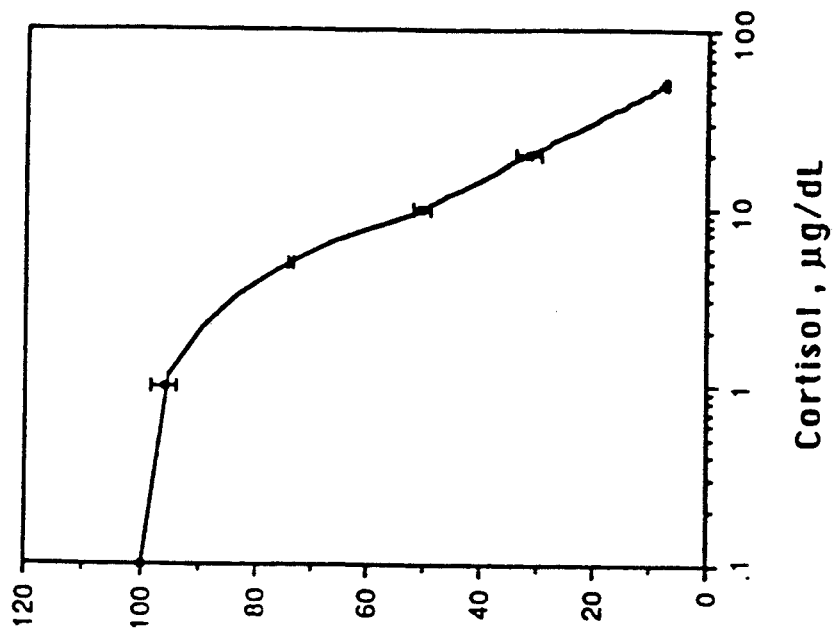
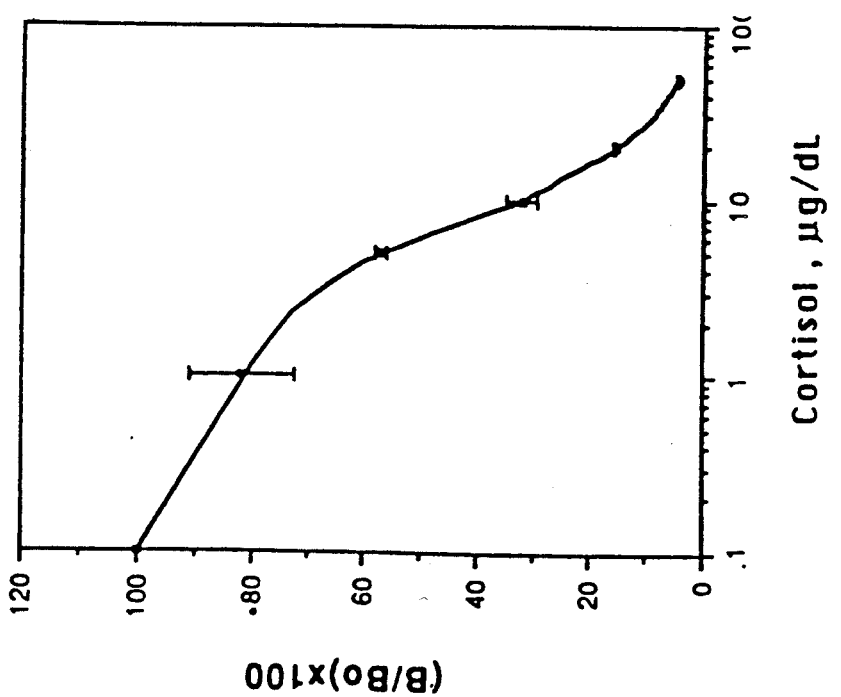

IMMUNOASSAY METHODS AND REAGENTS AND METHODS FOR PRODUCING THE LATTER

FIELD OF THE INVENTION

The present invention relates to immunoassay methods and reagents employing fluorescent chelates of lanthanide metal ions.

BACKGROUND OF THE INVENTION

The use of such chelates has numerous advantages. However, the known reagents and methods have not been as convenient and as effective as is desirable.

In applicant's Canadian patent application 488,513 filed Aug. 12, 1985, (European patent application 85305477.3, filed July 31, 1985) applicant has disclosed assays wherein immunoreactive substances are bound to a solid phase, the substances having connected to them as label or marker a moiety of a ligand which forms a fluorescent chelate with lanthanide metal ion. In order to measure the fluorescence of the chelate, the complex is dissociated with a dissociating solution to cause migration of the ligand from the solid phase to the bulk of the solution. The measurement of the fluorescence in solution results in loss of sensitivity, since the presence of liquid phase causes significant absorption and scattering of the excitation beam and of the emitted light.

Applicant is also aware of prior assay methods in which immunocomplexes are formed bound to a solid phase comprising substances having as marker or label ligands binding lanthanide metal ion, especially europium. In order to determine the quantity of europium which is bound, an enhancement solution is added which releases the europium from the ligand. The solution contains a further ligand which forms a fluorescent chelate with the europium in solution In addition to the disadvantages mentioned above, this method has the drawback that it is vulnerable to europium contamination from the environment of the laboratory or other surroundings, which gives an artificially elevated fluorescence reading in the presence of an excess of the development solution.

SUMMARY OF THE INVENTION

In accordance with an aspect of the invention, an immunoassay method comprises immobilizing immunoreactive substances on a solid phase. Complementary immunoreactive substances are reacted with the immobilized immunoreactive substances. The complementary immunoreactive bodies have connected thereto moieties of a ligand forming with lanthanide metal ion, a fluorescent chelate label wherein the metal ion is stably retained. The complementary immunoreactive substances bind to the immobilized immunoreactive substances. Any excess complementary immunoreactive substances are removed which are not bound to the immobilized substances. The fluorescence of the chelate label on bound complementary immunoreactive substances is measured in the presence of the metal ion stably retained with the chelate. A value is obtained indicative of the quantity of the complementary immunoreactive substances bound to the immobilized immunoreactive substances.

This method avoids the need for a step of dissociation of a labelled complex once formed on the solid phase, thus considerably simplifying the procedure. Since the fluorescence can be measured in the presence of an excess of lanthanide metal ion, the method is invulnerable to lanthanide metal ion contamination.

Preferably, the chelate is dried before its fluorescence is measured, thus alleviating problems of absorption or scattering of the excitation beam and of the emitted light. The method can be employed in sandwich or in competitive assay form.

In one preferred form, the complementary immunoreactive substance has connected to it, covalently or non-covalently (e.g. through a biotin-avidin or -streptavidin linkage), a moiety of a 1,10-phenanthroline-2,9-dicarboxylic acid disclosed in applicant's abovementioned Canadian and European applications, the disclosure of which is hereby incorporated by reference. The preferred moieties are represented as follows 1,10-phenanthroline-2,9-dicarboxylic acid compound selected from the group consisting of compounds of formula I:

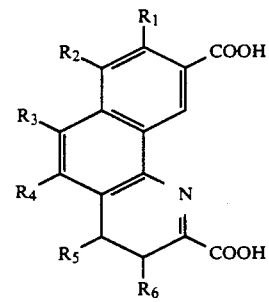

wherein:

each $R_1$ to $R_6$ group is independently hydrogen, $X(R_7)_n$ or $R_8$—, wherein X is $—SO_3^-M^+$ wherein M is metal ion or is a functional group which couples covalently with proteins or a group readily convertible to a functional group which couples covalently with proteins, $R_7$ is a divalent aliphatic residue having 1 to 12 carbons, or a divalent carbocyclic or heterocyclic residue having 3 to 12 carbons, and n is 0 or 1, and wherein $R_8$ is an aliphatic group having 1 to 12 carbons, or a carbocyclic or heterocyclic group having 3 to 12 carbons or one or more pairs of adjacent $R_1$ to $R_6$ groups form together with the carbons to which they are substituents (a) a carbocyclic or heterocyclic ring containing 3 to 12 carbons, (b) an X-substituted carbocyclic or heterocyclic ring of the general formula Ia:

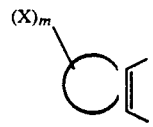

wherein 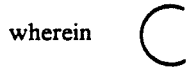

is a divalent carbocyclic or residue having 1 to 12 carbons, X has the signification given above, and m is an integer from 1 to 4, or (c) an orthoquinone linkage:

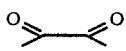

with the proviso that at least one of $R_1$ to $R_6$ is $X(R_7)_n$, wherein X, $R_7$, and n have the significations given above, or at least one pair of adjacent $R_1$ to $R_6$ groups form a ring of the formula Ia given above or an orthoquinone linkage, and trihalomethyl forms, salts, esters and acid halides thereof which are readily hydrolyzed to form the acid of formula I.

Applicant has found that such moieties of the 4,7-diphenyl-1,10phenanthroline-2,9-dicarboxylic acid form highly stable fluorescent chelates with lanthanide metal ion, preferably with europium metal ion, such that the metal ion remains stably attached to the solid phase and allows the assay to be conducted by measurement of fluorescence of the chelate bound to the solid phase. The invention is, however, by no means limited to use of the above-mentioned compounds. The suitability of other fluorescent chelates for use in the present method can be determined by trial and experiment having regard to the above principles and the detailed disclosure below.

Immunoreactive substances, especially antigens and antibodies, which are often desired to form the basis of reagents for immunoassay, are labile molecules. When they are reacted to introduce the residue of a ligand, they tend to become inactivated and to lose their properties of immunoreaction.

In a second aspect, the invention provides reagents for immunoassay and methods for making and using them whereby loss of immunoreactivity may be avoided or mitigated.

According to the said second aspect there is provided a reagent for immunoassay comprising a residue of an immunoreactive substance linked to a residue of a protein or polypeptide, the protein or polypeptide being labelled by substitution with a moiety of a ligand forming a fluorescent chelate with lanthanide metal ion.

With the reagents of the invention inactivation of the immunoreactive substance is avoided since the ligand-introducing reactant does not need to react directly with it.

Usually, in making the reagents of the invention, such reactant reacts with amino groups present on the protein or polypeptide. It has been found somewhat surprisingly that when a plurality of ligand moieties are introduced in each molecule of the protein or polypeptide, amplification of the fluorescent light emission can be achieved, as long as the Stokes shift of the fluorescent chelate (the difference between the wavelengths of maximum absorption of excitation radiation and of emitted light) is at least about 200 nm. It is suggested that with lower Stokes shifts, emitted light is reabsorbed by adjacent chelate moieties.

It is appreciated that the assay system of this invention can be adapted to detect a variety of biologically reactive matter. The system is particularly suited to detect a variety of haptens, antigen protein and antibody protein; for example, the immunoreactive body may be a hapten, such as cortisol, cortisol amine, thyroxine, digoxin or biotin. It may be an antigen protein such as α-fetoprotein (AFP), human chorionic gonadotropin (hCG), ferritin, thyrotropin (TSH), follitropin (FSH), lutropin (LH), thyroxine binding globulin (TBG), growth hormone or prolactin. It may be an antibody protein, such as monoclonal antibody to cortisol, antibody to AFP, antibody to hCG, or antibody to Rubella virus.

The protein or polypeptide of the reagent for the assay may comprise a carrier protein for example bovine serum albumin (BSA), thyroglobulin, polylysines of molecular weight 4,000 to 400,000, lysine copolymers with one or more of alanine, phenylalanine, serine, tyrosine, tryptophan and glutamic acid, having pendent amino groups on the polymer chain, hemocyanin, myosin, ferritin, catalase and reduced forms thereof.

The abovementioned immunoreactive substances may be linked to the abovementioned proteins and polypeptides by, for example, using a bifunctional reagent having one end group reactive toward groups which are present on one of the immunoreactive substance and the protein or polypeptide and not on the other, and a second end group which is reactive toward groups present on the protein or polypeptide but not on the immunoreactive substance. For example, the reagent may comprise sulfosuccinimidyl 4-(N-maleimidomethyl) cyclohexane-1-carboxylate (sulfo-SMCC) containing an amino group reactive N-hydroxy succinimide moiety at one end and a sulfhydryl group reactive maleimide moiety at the other. It may therefore be reacted with immunoreactive substances such as proteins, e.g. antibodies or antigens containing —$NH_2$ groups and free from -SH groups. To introduce maleimide moieties thereto, the resulting conjugate immunoreactive substances may be reacted with, for example, BSA which has been exhaustively reacted with a marker containing —$NH_2$ reactive groups so that all —$NH_2$ groups have been converted to ligand moieties and which has been reduced to create -SH groups from its intramolecular disulfide linkages. The -SH groups then react with the maleimide moieties.

In other procedures, the immunoreactive substance is reacted with a biotinylating agent to form a biotinylated derivative. A marker compound (for example as described in applicant's abovementioned patent applications) is reacted with avidin or streptavidin to provide it with pendent moieties of the ligand. The labelled avidin or streptavidin can then be reacted with the biotinylated substance under conditions allowing biotin-avidin or biotin-streptavidin association before or after an immunoassay is preformed with the biotinylated substance.

In an especially preferred form, avidin or streptavidin is employed having a plurality of the marker moieties on its molecule, thus achieving the light amplification effect referred to above.

Amplification may also be achieved in that a plurality of biotin moieties may be attached to the immunoreactive substance, whereby a plurality of the substituted avidin or streptavidin molecules will bind to the immunoreactive substance when the biotinylated component is reacted therewith.

Modifications and combinations of the above techniques may be employed. For example avidin or streptavidin may be linked to an immunoreactive substance through a bifunctional reagent, and a labelled carrier protein such as those mentioned above may be biotinylated and the biotin-avidin or biotin-streptavidin association may be formed therefrom. A biotinylated and labelled carrier protein may be employed, and in use may be linked through a sandwich type linkage, employing avidin or streptavidin as a central linking entity, to a biotinylated immunoreactive substance.

According to another aspect of the invention, processes are provided for making the above reagents which include the bifunctional linking reagent or the biotin/avidin or streptaviding linking reaction.

Preferably the marker labels employed are those described in applicants abovementioned patent application, but it will be appreciated that other markers may be employed.

The following Examples will be discussed with reference to the drawings wherein:

BRIEF DESCRIPTION OF THE DRAWINGS

FIGS. 2a and 2b show graphs plotting fluorescence and absorbance against fraction number;

FIGS. 3a and 3b show graphs plotting standard curves for cortisol assay by TRFIA;

DETAILED DESCRIPTION OF THE PREFERRED EMBODIMENTS

Figure 7C:
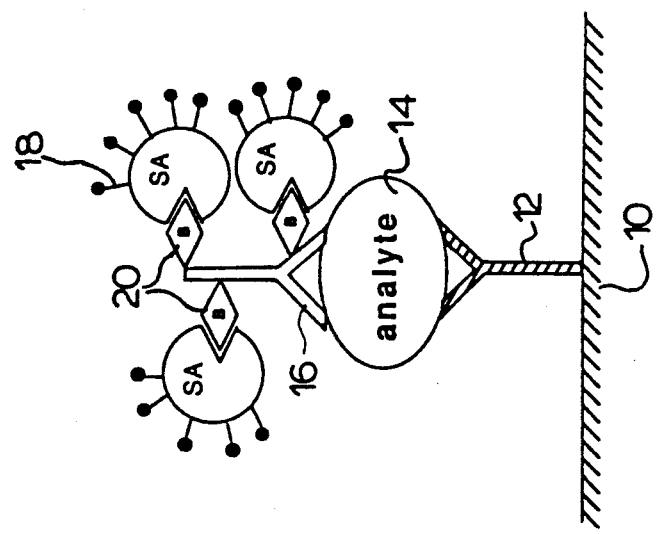
FIGS. 7a, 7b and 7c are diagrams illustrating various labelling techniques according to preferred embodiments of this invention for labelling immunoreactive bodies.
Figure 7B:
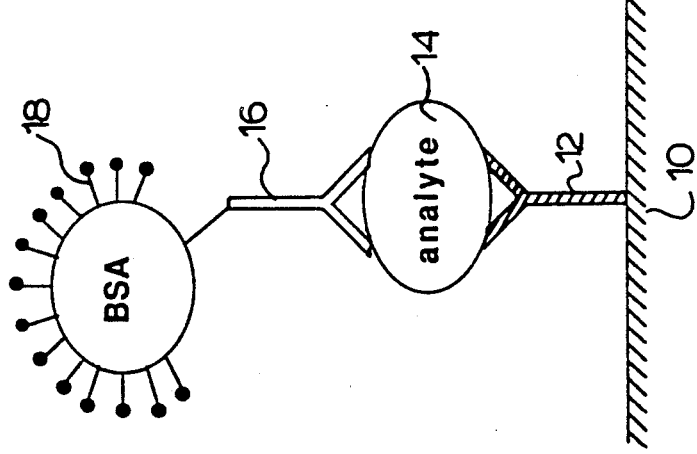
Figure 7A:
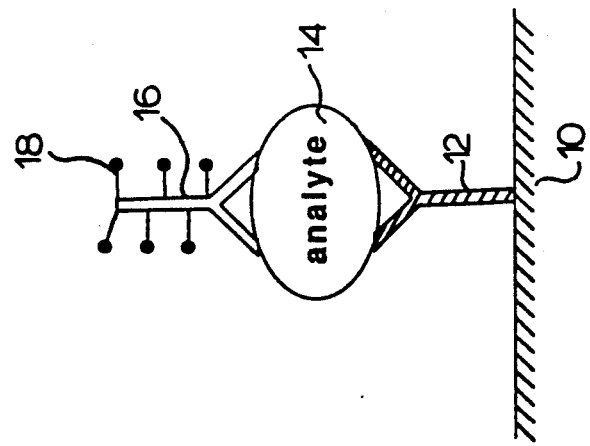

Before discussing in detail the following Examples, the various types of labelling systems, according to aspects of this invention, are shown in FIG. 7. In the discussion of FIG. 7 and with respect to other embodiments of the invention, it is appreciated that the terms immunoreactive body or bodies are the same as immunoreactive substance or substances and are used interchangeably throughout this specification. FIG. 7a shows a solid support 10 having bound thereto an immobilized immunoreactive body 12. The immunoreactive body may be an antibody specific to the analyte 14. A second immunoreactive body 16 specific to another site of the analyte 14 binds to the analyte. The second immunoreactive body may be a second antibody. The second antibody 16 has directly attached thereto the chelated fluorophors 18.

According to the embodiment of FIG. 7b, the second antibody 16 has a bovine serum albumin (BSA) molecule linked to the tail of the antibody 16. The linking element may be the reactant (sulfo-SMCC). The BSA molecule is, in turn, directly labelled with a plurality of the chelated fluorophors 18.

According to the embodiment of FIG. 7c, the second antibody 16 has a plurality of biotin molecules 20 attached thereto. A plurality of streptavidin molecules 22 have directly attached thereto, a plurality of fluorophors 18. The streptavidin molecules are therefore linked to the antibody 16 by the biotin molecules 20.

In each of these preferred arrangements of the assay system, the second immunoreactive body is labelled with stable fluorescent fluorophors 18 which, when subjected to stimulating energy, fluoresces to indicate the presence of the diagnostic immunoreactive body.

Examples of immunoassay methods, reagents and methods of producing them are given below.

EXAMPLE 1

Reagent and Assay for Cortisol

A carrier protein, bovine serum albumin (BSA) was first exhaustively labelled with a chelate, and then the labelled protein was cross linked to a molecule of an antibody with a bifunctional reagent. A heterogenous competition assay was then carried out for serum cortisol, with ovalbumin-cortisol conjugate immobilized in microtitration wells as the solid-phase.

Materials

Bovine serum albumin (BSA,RIA grade), ovalbumin, hydrocortisone 21-hemisuccinate and hydrocortisone 21-hemisuccinate BSA conjugate (cortisol-21-BSA) were purchased from Sigma Chemical Co., St. Louis Mo. 63178. Gelatin (EIA purity) was obtained from Bio-Rad Laboratories (Canada) Ltd , Mississauga, Ontario L4X 2C8 and Sephadex G25 medium mesh from Pharmacia (Canada) Ltd., Dorval, Quebec H9P 1H6. A radioimmunoassay (RIA) kit for cortisol, Cort-A-Count (trade mark) was purchased from Diagnostic Products Corp., Los Angeles Calif. 90045. 4,7-bis(chlorosulfophenyl)1,10-phenanthroline 2,9-dicarboxylicacid (Eurofluor S (trade mark) and hereinafter BCPDA) was synthesized according to the procedure described in applicants abovementioned patent application. Monoclonal antibody to cortisol was purchased from Medix Biotech Inc., Foster City Calif. 94404 and polyclonal rabbit anti cortisol (against cortisol-21-BSA) was purchased from Western Chemical Research Corp., Ft. Collins CO 80522. Protein concentration was carried out by centrifugation using Centricon (trade mark) 30 miroconcentrators from Amicon Canada Ltd., Oakville, Ontario L6H 2B9.

Enzyme immunoassay (EIA) microtitration plates were obtained from Flow Laboratories, Inc., McLean Va. 22102 and read on a EL309 microplate reader, Bio-Tek Instruments Inc., Winooski Vt. 05404. Fluoroimmunoassay (FIA) microtitration plates, Microfluor (trade mark) W, white opaque 96-well plates were purchased from Dynatech Laboratories, Inc., Alexandria Va. 22314 and read on the CyberFluor (trade mark) 615 Fluorometer.

High performance liquid chromatography (HPLC) was carried out using a BioSil TSK 400 size exclusion column from Bio-Rad Laboratories on a model 600 Gradient System equipped with a 490 variable wavelength detector (Waters, a division of Millipore (Canada) Ltd. Mississauga, Ontario L4V 1M5).

EXAMPLE 1(A)

Preparation of cortisol-ovalbumin conjugate. Cortisol ovalbumin was prepared by the mixed anhydride method. 50 mg (0.1 mmoles) of hydrocortisone 21-hemisuccinate were dissolved in 10 mL dixane and 0.1 mL tri-n-butylamine added. The solution was cooled to 10° C., 0.02 mL isobutyl chloroformate added and the mixture stirred for 30 min. Then, 500 mg of ovalbumin (0.01 mmoles) dissolved in 10 mL of water adjusted to pH 9 with NaOH were added to the reaction mixture and stirred 24 h at 4° C. After the reaction was completed, a precipitate was present. The mixture was dialyzed 36 h against water and the precipitate was removed by centrifugation. Urea was added to the supernatant to achieve a concentration of 6M and this solution was again dialyzed exhaustively against water. The protein concentration was determined by the Bio-Rad Protein Assay.

Conjugation of BCPDA to BSA. Two mL 0.5 M sodium carbonate buffer of pH 9.1 were added to 250 mg of BSA dissolved in 2 mL of water. 100 mg of BCPDA (50x molar excess) dissolved in 400 μL dimethylformamide (DMF) were added in 5 portions over a 15 min period. Unreacted BCPDA was removed by exhaustive dialysis against 0.1 M $NaHCO_3$ and the labelled BSA (BSA-BCPDA) stored at 4° C.

Reduction of BSA-BCPDA: Reduction was carried out just prior to conjugation with antibody. To BSA-BCPDA (30 mg/mL in 0.1 M $NaHCO_3$) solid urea, dithiothreitol (DTT) and Tris base were added to achieve a concentration of 6 M, 50 mM and 0.1 M respectively. The pH measured was 9: The mixture was incubated for 1 h at 37° C.

EXAMPLE 1(B)

Conjugation of antibody and reduced BSA-BCPDA: Conjugation with sulfosuccinimidyl 4-(N-maleimidomethyl)-cyclohexane-1-carboxylate (sulfo-SMCC) was carried out by a modification of the method of Yoshitake et al, *European Journal of Biochemistry*, 1979, Vol. 101, pp 395 to 399. 0.5 mL of anti-cortisol antibody solution (1 mg/mL) was dialyzed overnight against 0.1 M sodium phosphate buffer of pH 7.0 14.5 μL of a 5 mg/mL solution of sulfo-SMCC dissolved in the same buffer was added and the solution shaken for 1 h at room temperature. Unreacted sulfo-SMCC was removed by desalting on a 25 mL column of Sephadex G 25 using 0.1 M sodium phosphate of pH 6.2 containing 5mM ethylenediaminetetraacetate (EDTA) as the elution buffer. The fractions containing protein were combined and concentrated to 0.1–0.2 mL by centrifugation in a Centricon 30 device. 0.35 mL of reduced BSA-BCPDA containing 9 mg of protein was also desalted to remove excessive reducing agent on a 25 mL Sephadex G25 column in the same phosphate buffer of pH 6.2, containing 5 mM EDTA, to retard disulfide formation. The protein containing fractions were combined and concentrated by centrifugation in a Centricon 30 device, to 0.6–0.8 mL. It is important to complete the reactions and the separation and concentration steps as quickly as possible to prevent hydrolysis of the maleimide group in the antibody and reformation of the disulfide bonds in the reduced BSA. The derivatized antibody and reduced BSA were combined and incubated 20 h at 4° C. (BSA to IgG ratio is ~30–40 fold). Prior to purification of the IgG-BSA conjugate, excess SH groups on the reduced BSA molecule (36 SH groups exist per reduced BSA molecule) were blocked by addition of a two-fold excess of N-ethylmaleimide in DMF and incubation for 1 h at room temperature.

Isolation of BSA-conjugated antibody: The conjugated and unconjugated antibody and unconjugated labelled BSA were separated by size exclusion HPLC on a BioSil TSK 400 column (300×7.5 mm) eluted at 1 mL/min with 50 mM $Na_2SO_4$, 20 mM sodium phosphate pH 6.8 and fractions of 0.5 mL were collected automatically. 3 or 4 injections of 250 μL each were required per preparation to complete the isolation. Fractions were analyzed for total fluorescence, fluorescent antibody, and total antibody concentration, as described below.

Total fluorescence was measured by addition of 200 μL of $10^{-5}$M $Eu^{3+}$ solution in 50 mM Tris buffered saline pH 7.8 (TBS) to 5 μL of each fraction and determining the fluorescence of the solution after 5 minutes, on an 'ARCUS' gated fluorometer (LKB Wallac, Turku, Finland).

To measure the BSA-conjugated antibody concentration, 100 μL of fractions diluted 1/20 and 1/200 in 1% BSA in TBS, were added to the wells of coated Microfluor W plates. Coating was done overnight at 4° C. with 100 μL per well of a 5 μg/mL solution of cortisol-BSA conjugate in 0.1 M sodium bicarbonate and afterwards the plates were blocked for 1 hour at room temperature with 1% BSA in the same buffer. The plates were incubated 1 hour at 37° C. and then washed 3-4 times with water. 100 μL of $1 \times 10^{-5}$M $Eu^{3+}$ solution in TBS was then added. After 5 min, the plates were washed once with water and dried in a stream of cool air. Surface fluorescence of the antibody-BSA-BCPDA $Eu^{3+}$ conjugate which was bound to the immobilized cortisol-BSA was measured in a CyberFluor 615 fluorometer.

The total antibody activity (conjugated to BSA and unconjugated) was measured using a second antibody (anti rabbit IgG or anti mouse IgG for polyclonal or monoclonal anticortisol, respectively) coupled to horseradish peroxidase (HRP) in an ELISA assay. EIA plates were coated with cortisol-BSA conjugate and blocked as above. HPLC fractions were diluted, added to the EIA plate and incubated at 37° C. as above. After washing with water, 100 μL horseradish peroxidase labelled goat anti rabbit or anti mouse IgG diluted 1/500 with 50 mM sodium phosphate pH 8.5 containing 1% NaCl and 1% BSA were added and incubated a further hour. The plates were washed with water and the enzymatic activity of the bound antibody-anti-IgG- HRP complex bound to immobilized cortisol-BSA was measured by adding 100 μL of substrate (1 mg/ml of ABTS in 50mM $Na_2HPO_4$, 25 mM citric acid, 0.03% $H_2O_2$). The optical density was determined on a microplate reader after 5–10 minutes.

EXAMPLE 1(c)

Cortisol assays: A solid phase competition assay was used with immobilized antigen to measure cortisol. Microfluor W plates were coated overnight at 4.C with 100 μL of 2 μg/ml cortisol-ovalbumin conjugate in 0.1 M $NaHCO_3$. The plates were rinsed once with water and blocked for 1 hour at room temperature with 0.1% gelatin, 0.1% Tween 20,50 mM phosphate buffer of pH 7.4 and stored in the same solution at 4° C.

Before the assay, a plate was washed twice with 0.05% Tween 20 in saline (Tween/NaCl) and twice with water. Antibody (labelled BSA-conjugated antibody prepared as in Example 1(b)) was diluted to 1/400 with respect to the starting material (1 mg/mL) in TBS containing 0.3 M trichloroacetic acid (TCA), 1% BSA and 150 μg/mL BSA-BCPDA to prevent possible fluor-serum interactions. 10 μL of serum was pipetted into the wells and 100 μL of antibody solution added. The plate was briefly shaken and incubated 1 h at 37° C. The plate was washed three times with Tween/NaCl and twice with water, then 100 μL of $1 \times 10^{-5}$M $Eu^{3+}$ in TBS was added. After five minutes, the plate was rinsed once with deionized water, dried with a stream of cool air and surface fluorescence of the dry solid determined on a CyberFluor 615 fluorometer.

RESULTS

Conjugation of Antibodies

In the coupling scheme which is used to conjugate BSA-BCPDA to antibody, the antibody, which has no free sulfhydryl groups, is reacted with a bifunctional coupling reagent containing an amino reactive N-hydroxy succinimide moiety at one end and a sulfhydryl reactive maleimide group at the other end. The sulfonic acid group renders the reagent water soluble. The reagent is reacted first with the antibody to introduce maleimide groups (step 1). The BSA which has been exhaustively reacted with BCPDA (step 2) is reduced with DTT to create free sulfhydryl groups from intramolecular disulfide bonds in the native molecule (step 3). The exposed SH groups are then free to react with the maleimides introduced into the antibody (step 4).

Figure 1B:
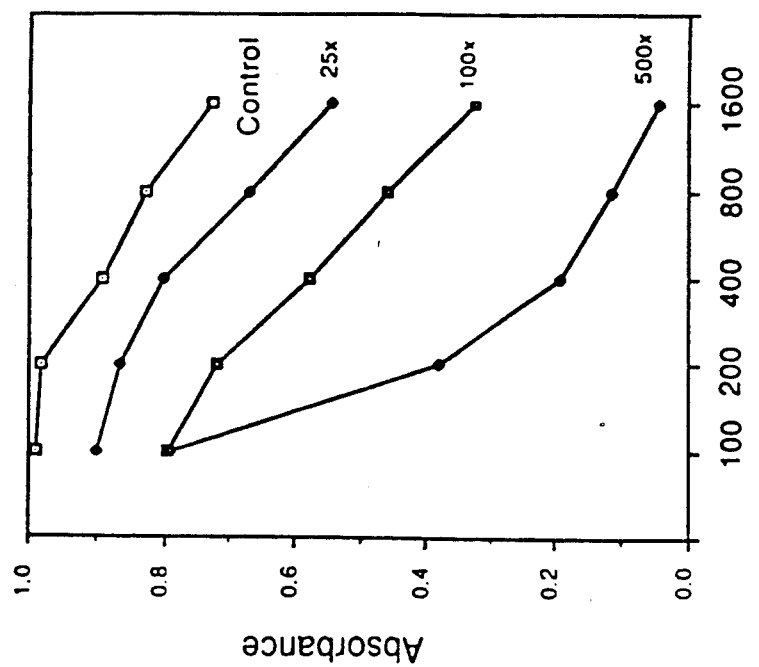
FIGS. 1a and 1b show graphs plotting absorbance against 1/dilution for titres of polyclonal anticortisol antibodies and monoclonal anti-cortisol antibodies, respectively, after modification with sulfo SMCC.
Figure 1A:
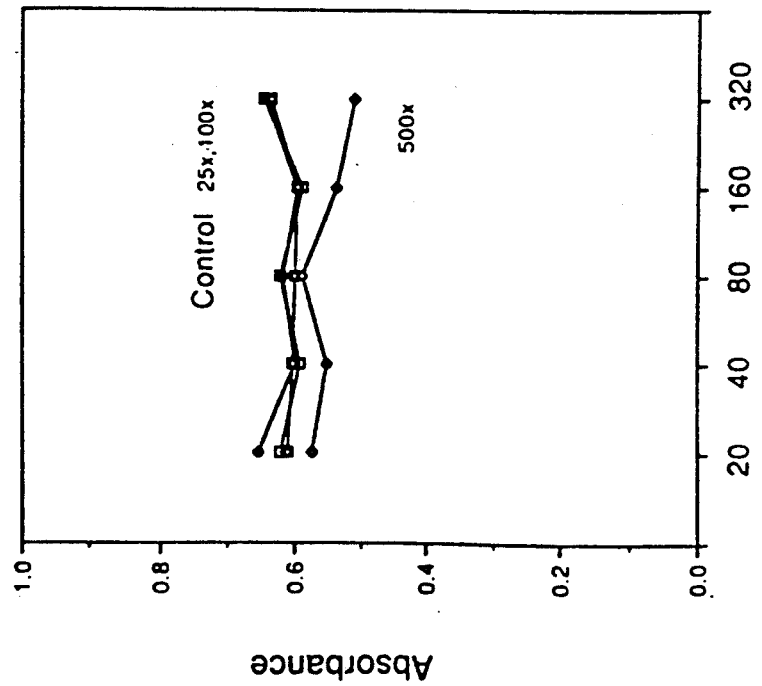

Since it is possible to get inactivation of antibody at high concentrations of coupling reagent, the effect of the concentration of coupling reagent in step 1 on the activity of the final conjugated antibody preparation was studied using both a polyclonal and a monoclonal anti cortisol antibody. Antibodies were reacted for 1 hour at varying molar excess of sulfo-SMCC in step 1. The titre of the modified but unconjugated antibody was measured by ELISA, by on the HPLC fractions using an HRP conjugated anti IgG in microtitration plates as described in methods (isolation of conjugated antibody). As shown in FIG. 1 the monoclonal antibody preparation was highly active even after derivatizing with 500-fold excess of sulfo-SMCC, the polyclonal antibody inactivation was evident even at 25-fold molar excess of sulfo-SMCC (FIG. 1b). The monoclonal, was therefore treated with a 50-fold molar excess of sulfo-SMCC while the polyclonal was treated with a 20-fold excess, in step 1. Because of the possibility of cross linking networks in step, 4 due to the reaction of one BSA molecule bearing many SH groups with multiple molecules of derivatized antibody and also, of one derivatized antibody molecule with multiple molecules of reduced BSA, the reduced BSA/derivatized antibody molar ratio was selected to be very high (>25 fold) so as to promote formation of IgG(BSA)n rather than BSA(IgG)n.

After conjugation, the conjugated and unconjugated antibody were separated by gel filtration on HPLC. The fractions were monitored for optical density, total fluorescence, fluorescent antibody binding to cortisol-BSA coated plate and total antibody binding to cortisol-BSA coated plates, using a second peroxidase conjugated anti IgG antibody in an ELISA assay as described in Material and Methods. The results of a typical monoclonal preparation is shown in FIGS. 2a and 2b. There is a continuous spectrum of fluorescent antibodies present with different molecular weights, with a large fraction in the void volume. There are three peaks of total antibody activity as measured by the ELISA technique (FIG. 2b), the void volume (peak A), an included peak also corresponding to coupled antibody (peak B) and an included peak corresponding to uncoupled antibody (peak C). Only peak A and the first fractions of peak B were combined for use in the assays so as to ensure that essentially all uncoupled antibody is excluded. Assuming that the binding of the second antibody HRP-conjugated anti IgG is similar for all the fractions of anti cortisol, irrespective of the degree of conjugation to BSA, 30-50% of the antibody is recovered in the conjugated antibody fractions combined and used for the immunoassay.

Assay optimization

An outline of the cortisol competition assay is shown in FIGS. 3a and 3b. The calibration curves for the cortisol assays were plotted with the ratios of the fluorescence of the standards, B, to the fluorescence of the zero standard, $B_o$, expressed as a percentage, $(B/B_o \times 100\%)$ were plotted vs the log of the cortisol concentration. FIG. 3a shows the results for a 20 µL sample volume, whereas FIG. 3b shows the results for a 10 µL sample volume per well.

Variation in the amount of coating in the microtitration wells from 50 to 500 ng of cortisolovalbumin conjugate had little effect on the overall shape of the calibration curve when this is plotted as $(B/B_o)$ but the total antibody bound to the plate (proportional to $B_o$) reached its maximum at a coating of 200 ng/well. It was found that calibration curves with the conjugated polyclonal antibody became flat with no further change in $(B/B_o \times 100)$ when this value reached 30%, regardless of increasing cortisol concentration whereas the curves with conjugated monoclonal continued to drop until a value of $(B/B_o \times 100)$ close to zero was obtained. Continued experimentation was thus conducted exclusively with the monoclonal antibody.

Since >80% of the cortisol in serum is bound to transport proteins, a suitable dissociation reagent is required to release the cortisol before measurement by immunoassay. Using monoclonal antibody, two reagents were investigated: 8-anilino-1-naphthalene sulfonic acid, ANS, at a concentration of 5% in the final assay mixture and trichloroacetic acid, TCA as disclosed in Eskola et al, Clin. Chem. 1985 31, pp 1731-1734, at a concentration of 0.3 M. TCA gave better results than ANS and thus it was preferred in the final assay design. The volume of serum required in order to obtain sensitive calibration curves was tested. This parameter affected the shape of the calibration curve dramatically. The normal range of cortisol in human serum is 5-30 µg/dL. Using 20 µL of serum, it was found that the curves were too shallow at concentrations greater than 20 µg/dL. A better calibration curve is obtained with 10 µL sample volume. With 10 µL serum (FIG. 3b) good sensitivity was achieved in the whole range of clinically important values, (1-50 µg/dL).

Assay Performance

A typical calibration curve is shown in FIG. 3b. The steepest part of the curve is in the normal range where maximum accuracy and precision is usually needed.

The within run precision for four patient samples had C.V.'s of 2-10%. This kind of precision is typical for well established cortisol assays currently available.

To test the linearity of the method patient samples were diluted with the zero standard and reassayed. For samples with cortisol concentration less than 50 µg/dL, there was a linear relationship between the measured concentration and the dilution. Above 50 µg/dL, the assay cannot accurately measure samples, giving readings between 50 and 60 µg/dL regardless of the concentration. This underestimation of concentration was also true for the RIA assay. After the first two-fold dilution of samples with concentration >50 µg/dL, which brings the concentration to within the sensitivity of the standard curve, diluting the sample further also resulted in a linear relationship indicating that this was not a serum effect.

The recovery of added cortisol was measured in five different samples. The recovery of cortisol varied from 91% to 115%, with a mean of 102%.

27 patient samples were measured by a commercial RIA kit (Diagnostic Products Corp.) as well as with the present method with conjugated fluorescent monoclonal antibody. The samples were selected to cover the whole range of the assay from 1 to 50 μg/dL and included clear, cloudy, lipemic, and haemolytic specimens. The correlation between the two assays was good. The coefficient of correlation was 0.98 with a slope of 1.007 and an intercept of 0.51 μg/dL.

EXAMPLE 2

Methods and reagents for a sensitive noncompetitive sandwich immunofluorometric assay (IFMA) for the determination of AFP in serum and amniotic fluid.

A monoclonal antibody was non-covalently immobilized in a microtiter strip (or plate) well. A biotinylated affinity purified antibody was used as the detection antibody and streptavidin labelled with BCPDA, was used as the fluorescent label The complex consisting of monoclonal antibody-AFP-polyclonal antibody-biotin-streptavidin-BCPDA-$Eu^{+3}$ was quantitated on the dry surface of the well by excitation with a nitrogen laser beam and monitoring the specific delayed fluorescence at about 615 nm.

EXAMPLE 2(a)

Biotinylation of antibody

Affinity-purified goat anti-AFP antibody (Atlantic Antibodies, Scarborough, ME 04074, cat. no. 077-06) was dialyzed twice against 5 L of saline and then diluted in 0.1 mol/L carbonate buffer, pH 9.0 to a final concentration of 500 μg/mL. To 1 mL of this solution, a 500-fold molar excess of sulfosuccinimidyl 6-(biotinamido) hexanoate (NHS-LC-biotin, Pierce Chemical Co., Rockford, Ill. 61105) dissolved in 100 μL of dimethylsulfoxide (DMSO) was added. After mixing and incubation for 1 h at room temperature, the reaction mixture was dialyzed twice at 4° C. against 5 L of 0.1 mol/L carbonate buffer, pH 8.3 containing 0.025% (w/v) sodium azide.

The biotinylated antibody solution was diluted 1:300 in 10 mmol/L Tris-HCl buffer, pH 7.8 containing per liter 400 mmols KCl, 10g BSA, 0.1 g sodium azide and 0.1 g thimerosal before use.

EXAMPLE 2(b)

Preparation of labelled streptavidin

Five mg of streptavidin (Sigma) were dissolved in 33 mL of 0.1 mol/L carbonate buffer, pH 9.1. Seven mg of BCPDA dissolved in 200 μL dimethylformamide were added to the streptavidin solution with stirring, at room temperature. Alternatively, 200 μL of absolute ethanol may be used as the solvent. In this circumstance, only 2 mg of BCPD is required. After 1 h, the reaction mixture was dialyzed three times against 5 L of 0.1 mol/L solution of $NaHCO_3$, containing 0.025% (w/v) sodium azide.

The labelled streptavidin solution was diluted 1:50 in 50 mmol/1 Tris-HCl buffer, pH 7.8 containing per liter 10 g BSA, 9 g NaCl, 0.1 g sodium azide, 0.1 g thimerosal and $Eu^{3+}$ at a final concentration of $10^{-5}M$ before use.

EXAMPLE 2(c)

Immunoassay

AFP standards

Human AFP (InterMedico, Toronto, Canada) was calibrated against the international reference standard (72/227) for AFP. AFP standards covering a range from 1 to 1000 IU/mL were prepared in the standards diluent solution.

Patient samples and controls

Sera from pregnant women at various gestational ages, amniotic fluids and sera from patients with liver and testicular tumors were obtained from the Toronto General Hospital Quality control human based sera were Tri-level ligand controls from Ortho Pharmaceuticals, Toronto, Canada. Amniotic fluid was diluted 100 fold in standards diluent solution before analysis.

Comparative methods

A commercially available radioimmunoassay procedure (Amersham Corp., Arlington Heights, IL 60005) and a time-resolved immunofluorometric procedure (DELFIA hAFP kit, LKB Wallac, Turku, Finland) were used. Both procedures were carried out using the manufacturer's instructions.

Preparation of microtiter wells (8 or 12 - well strips or 96-well plates). Polystyrene white microtiter wells (MicroFluor, Dynatech Laboratories, Alexandria, Va. 22314) were coated with 200 ng/100 μL/well purified monoclonal anti-AFP antibody (Medix Biotech Inc., Foster City Calif. 94404, cat. no. A-013-01) dissolved in 50 mmol/L carbonate buffer, pH 9.6, for 18-20 h at 4.C. After coating, the wells were washed manually two times with wash solution. Tris-buffered saline (TBS), pH 7.5, containing 0.05% (v/v) Tween 20. The wells were then blocked with 200 uL/well of blocking solution (0.1 mol/L solution bicarbonate, pH 8.3, containing 1% (w/v) bovine serum albumin (BSA, RIA grade Sigma Chemical Co., St. Louis, Mo. 63178), 2% (w/v) sucrose and 0.05% (w/v) sodium azide) for 1 h at room temperature. The wells were washed again as described above and stored dry at 4° C.

Immunoassay procedure

Twenty μL of standards or samples (duplicate or preferably triplicate measurements) were added to each well followed by the addition of 100 μL standards diluent buffer. After the wells were incubated for 45 min at 37° C. (air oven), the wells were washed twice with the wash solution 100 μL/well of the 1:300 dilution of biotinylated anti-AFP antibody solution were then added, the wells incubated for another 45 min at 37° C. and then washed as above. 100 μL/well of the mixed labelled streptavidin- $Eu^{3+}$ working solution were then added and the wells further incubated for 30 min at 37° C. The wells were then washed as above and dried using a forced air plate dryer. The fluorescence was measured on the solid phase in a CyberFluor 615 time-resolved fluorometer/analyzer using an excitation wavelength of 337.1 nm (nitrogen laser source) and an emission wavelength of 615±5 nm (interference filter).

RESULTS

Incubation Time and Temperature

The effect of the incubation time and temperature on the performance of the AFP assay were investigated. The quality of the calibration curve, the precision of the assay and the accuracy of measurements were monitored by analyzing a series of 20 clinical samples previously assayed for AFP by RIA. It was found that a precise and accurate assay could be established if the incubation times were fixed at 45, 45 and 30 min, at 37° C. With this choice, an assay run could be completed in less than 3 h.

Sensitivity and Precision

The assay had a dynamic range of 1–1000 IU/mL (0.97–970 ng/mL) and a detection limit of 0.1 IU/mL, as calculated from the mean fluorescence +3 standard deviations of the zero standard. At concentrations of analyte >1000 IU/mL, the curve of a log-log plot is relatively flat and cannot be used for analytical purposes.

Precision studies were performed using tri-level commercial control sera. As shown in Table I, the intra-assay coefficients of variation (CVs) for AFP levels of 21.5, 58 and 170 IU/mL were 7.6, 5.4 and 6.2%, respectively. Inter-assay CVs for the same controls were 3.9, 8.6 and 1.7%, respectively. Day-to-day precision was also determined over a one month period for the same controls and found to be 7.2, 7.3 and 8.7%, respectively.

Recovery and Linearity

To assess the recovery of the assay, spiked serum samples were prepared by adding various concentrations of AFP to 9 pooled serum specimens (9 different additions in each, 100 or 200 IU/mL). The analytical recovery of AFP ranged from 72 to 125% with a mean of 104±17%.

To evaluate the linearity of the assay, serial dilutions of 3 different samples were tested and the amount of AFP in each sample determined The concentration of AFP decreased linearity with increasing dilution, and values obtained were those expected, if the value of the undiluted sample is taken as a true value. This finding confirms that the assay is free of any serum matrix effects.

Correlation Studies

A comparison study with a commercial RIA kit of 104 maternal serum and 20 amniotic fluid samples from women at various gestational ages was undertaken. Correlation plots were made for maternal serum AFP and amniotic fluid AFP respectively. Correlation coefficients of r=0.95 and r=0.92 were achieved for serum and amniotic fluid, respectively. In addition, the present assay was evaluated with a commercial time-resolved fluoroimmunoassay kit (TR-FIA). Good correlation (r=0.90) was observed when 90 serum samples were tested in both assays.

TABLE I

Precision Studies with α-Fetoprotein Assay using commercial human serum-based quality control sera.

| Sample | AFP (IU/mL) Mean | SD | % CV | Replicates |
|---|---|---|---|---|
| Intra-assay | | | | |
| I | 21.5 | 1.6 | 7.6 | 21 |
| II | 58.0 | 3.1 | 5.4 | 21 |
| III | 170.0 | 10.5 | 6.2 | 21 |
| Inter-assay | | | | |
| I | 21.0 | 0.8 | 3.9 | 4 |
| II | 68.0 | 5.9 | 8.6 | 4 |
| III | 179.0 | 3.0 | 1.7 | 4 |
| Day-to-day | | | | |
| I | 19.1 | 1.4 | 7.2 | 11 |
| II | 68.4 | 5.0 | 7.3 | 10 |
| III | 171.7 | 14.9 | 8.7 | 10 |

EXAMPLE 3 an immunofluorometric assay for the determination of hCG in serum. The assay was based on the sandwich principle, and was performed in microtiter wells coated with a monoclonal antibody to hCG beta-subunit as the solid phase, and biotin-labelled monoclonal to intact hCG as the detection antibody. The degree of binding of the biotinylated antibody to captured hCG molecules was determined covalently attached to streptavidin. The fluoroescene of the final complex formed (Antibody1-hCG-Antibody-2-Biotin-Streptavidin-BCPDA-$Eu^{3+}$) is then quantitated, in the dried solid phase, by pulsed fluorescence measurements using the CyberFluor 615 gated fluorometer/analyzer.

MATERIALS AND METHODS

1. Reagents and Buffers

Human TSH (specific activity, 6.6 IU/mg), human FSH (specific activity, 6200 IU/mg), and human LH (specific activity, 5000 IU/mg), were obtained from Sigma Chemical Co., St. Louis, Mo. 63178. Bovine serum albumin, bovine globulin and streptavidin (cat. no. S-4762) were also from Sigma.

The coating buffer was 0.01 mol/L Tris, pH 8.25, containing 0.1 mol/L NaCl. The blocking buffer was 0.1 Mol/L carbonate, pH 8.3, containing 1% BSA and 0.05% sodium azide. The assay buffer was 0.05 mol/L Tris, pH 7.8, containing 0.15 mol/L NaCl, 0.05% sodium azide, 0.5% BSA, 0.05% bovine globulin and 0.01% Tween 40. The streptavidin-europium buffer was 50 mmol/L Tris, pH 7.8, containing 0.15 mol/L NaCl, 1% BSA, and 0.5% sodium azide. The wash solution was 0.15 mol/L NaCl, containing 0.05% Tween 20, and 0.05% sodium azide.

2. hCG Standards

Purified hCG (specific activity, 3310 IU/mg in terms of the first IRP, 75/537, for immunoassay) was obtained from Calbiochem, Behring Diagnostics, La Jolla, Calif. 92037. The preparation was reconstituted according to the manufacturers recommendation, and diluted in hCG-free human serum (Chemicon International Inc., El Segundo, Calif. 90245) to give the desirable standard concentrations.

3. Monoclonal Antibodies

Monoclonal antibody to beta-subunit of hCG (cat. no. H-298-12), and to intact hCG molecule (cat. no. H-296-01), where DEAE-column chromatography purified immunoglobulin fractions, purchased from Medix Biotech Inc., Foster City, Calif. 94404. The degree of cross-reactivity of these antibodies, as determined by the manufacturer in a conventional RIA, were: hCG 100%, hCG beta 100%, hCG alpha 0.0%, hLH 0.3%, and hTSH 0.02% for the antibody to the beta-subunit of hCG; and hCG 100%, hCG beta 0.0%, hCG alpha 0.0%, hLH 90%, hTSH 85%, and hFSH 16% for the antibody to intact hCG molecules. A monoclonal antibody to human LH(hLH) was also obtained from Medix Biotech (Cat. no. L-461-01).

4. Specimens

Human serum samples containing various concentrations of hCG were provided by Hospital Incommon Laboratory, Toronto, Canada. These samples were from pregnant and non-pregnant females, and had been stored at −20° C. To exclude any possible effect of storage on hCG concentrations, the samples were concurrently tested with the present method and the comparative kits. Specimens exceeding 500 IU hCG/L were diluted with hCG-free serum to bring them within the measurement range of the assay. Lyphochek immunoassay control serum (human) levels I, II and III were from Bio-Rad Clinical Division, Richmond, Calif. 94801.

5. Comparative Methods

Two commercially available kits were used as comparative methods. The EchoClonal hCG Assay (Bio-Rad) was a sandwich type immunoradiometric (IRMA) procedure. It uses solid-phase monoclonal anti-hCG antibodies bound to immunobeads, and Iodine-125 labelled monoclonal anti-hCG antibodies as the tracer. This assay is a single reagent procedure, combining the solid phase and the tracer in a tracer/immunobead reagent. The counting of radioactivity and data reductions were performed with the LKB-Wallac (Turku, Finland) 1275 Minigamma counter.

The DELFIA hCG Assay (LKB-Wallac) was a time-resolved immunofluorometric procedure. As the solid phase it uses a monoclonal antibody to hCG beta-chain immobilized into wells of microtiter strips. The tracer is a monoclonal anti-hCG alpha-subunit labelled with europium. The measurement of fluorescence was performed on a LKB 1230 Arcus fluorometer.

Both kits were calibrated against the World Health Organization (WHO) first international reference preparation (IRP 75/537) for immunoassay. Procedures recommended by the manufacturers were followed for duplicate measurements of the specimens.

EXAMPLE 3(a)

Biotinylation of Antibody

The monoclonal antibody against hCG intact molecule (Anti-hCG) was biotinylated according to the following procedure. A 0.5 mL aliquot of the antibody solution (1 mg/mL in 0.015 mol/L potassium phosphate buffer pH 7.2 containing 0.15 mol/L NaCl and 0.1% NaN3) is mixed with 0.5 mL of a carbonate/bicarbonate buffer (0.1 mol/L, pH 9.0). To the mixture is then added a 500-fold molar excess of NHS-LC-Biotin dissolved in 100 μL of distilled water (dH20), and incubated at room temperature for 30 minutes. The unconjugated biotin is then removed by dialysis in tubing with $M_r$-10000 cutoff at 4° C. for 24 hours against several changes of 0.1 mol/L sodium bicarbonate pH 8.3 containing 0.05% sodium azide. The biotin- anti-hCG conjugate was then titrated to determine the optimal concentration for the assay, and stored at 4° C. Prior to use the antibody is diluted with the assay buffer to give a working dilution of 1 to 100.

EXAMPLE 3(b)

Labelling of Streotavidin with BCPDA

Affinity purified streptavidin (Sigma) was dissolved in 0.1 mol/L carbonate/bicarbonate buffer, pH 9.1, to obtain a concentration of 0.15 mg/mL. To an aliquot of this preparation was then added a 50-fold molar excess of BCPDA dissolved in N,N-dimethylformamide (Sigma) at a concentration of 35 mg/mL. As exemplified in Example 2(b), the alternative solvent, absolute ethanol, may be used resulting in the use of less BCPDA. After 1h incubation at room temperature, the mixture was dialyzed against three changes of 0.1 mol/L sodium bicarbonate, pH 8.3, containing 0.05% sodium azide. This preparation was stored at 4° C.

EXAMPLE 3(c)

Assay

Immobilization of Anti-hCG β-Subunit

The monoclonal antibody to hCG β-subunit (anti-hCG-beta) was immobilized by adsorption onto wells of microtiter plates or strips. The coating was prepared by adding 100 μL per well of anti-hCG-beta monoclonal antibody prepared at a concentration of 5 μg/mL in the coating buffer. After overnight incubation at 4° C., the wells were washed 5 times with the wash solution, and then 2 times with H20. To block the remaining active sites, 200 μL of the blocking buffer were then added and allowed to incubate at room temperature for one hour followed by storage at 4° C. Prior to use the plates were washed 2 times with wash solution.

Assay Procedures

Biotinylated monoclonal antibody was diluted with the assay buffer to a concentration of 5 μg/mL. 50 μL duplicates of hCG standards or serum samples and 50 μL of biotinylated antibody solution were then pipetted into microtiter wells. After shaking the wells for three minutes by means of an automatic shaking device, they were allowed to incubate at room temperature for two hours. The reaction mixture was then removed, and the wells were washed four times with the wash solution using a multi-channel pipette. Binding of biotinylated antibody to hCG was determined by addition of 100 μL per well of the indicator reagent containing BCPDA labelled streptavidin (1.5 μg/mL) and $EuCl_3$ ($10^{-5}$ mol/L). The indicator reagent was prepared by diluting (1:100) the stock preparations of BCPDA conjugated streptavidin (0.15 mg/mL) and of europium (1 mmol/L in 0.01 N HCl) with the strepavidineuropium buffer. After 45 minutes incubation at room temperature, wells were washed twice with washing solution, dried for 5 minutes by means of a forced air plate dryer, and the fluorescence at the bottom of the dried wells was measured by the CyberFluor 615 fluorometer.

RESULTS

Detection Limit and Dynamic Range of the Assay

Figure 4:
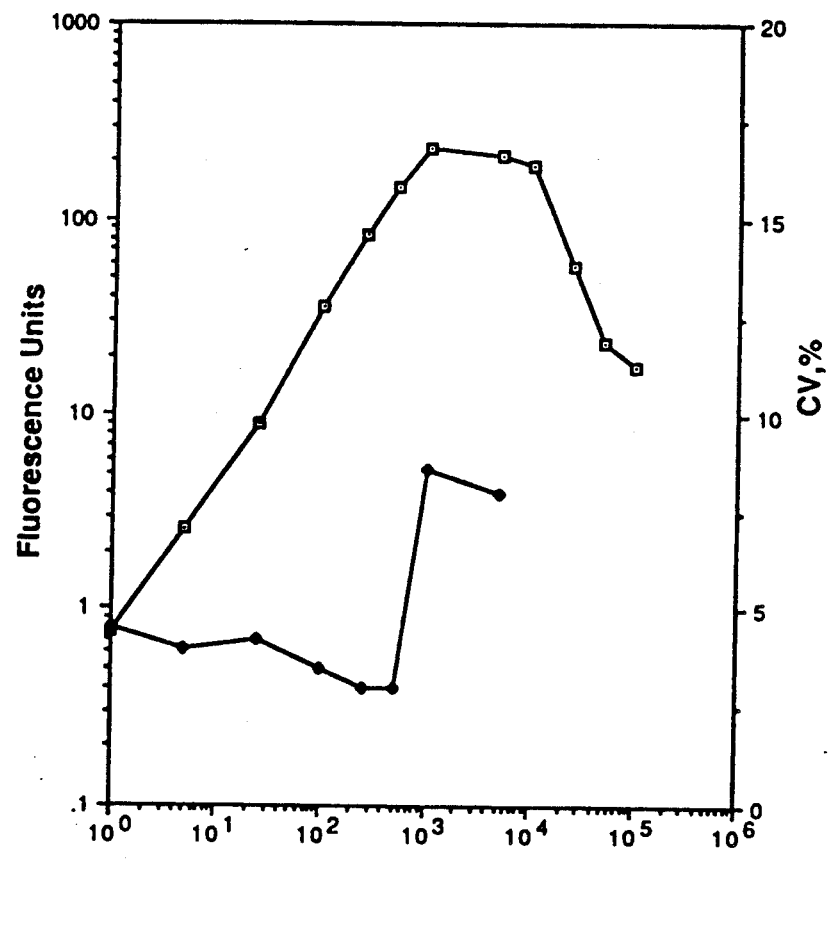
FIG. 4 shows a dose-response curve, and precision profile of an hCG assay.

A typical dose response curve obtained with the assay is presented in FIG. 4. Points represent mean fluorescence values of duplicate measurements from which the mean value of zero standard is subtracted. A linear relationship between the response and standard dose exists in the 1 to 500 IU hCG/L concentration range.

Using the value corresponding to the mean plus three standard deviations (SD) of the zero standards, the detection limit of the assay appeared to be less than 1 IU/L. However, when calculated as 3 SD of the mean for 15 determinations of the zero hCG standard, the detection limit was about 1.5 IU/L. The background fluorescence of the zero standard is about 6.5±0.35 units.

The working range of the assay was established according to a precision profile derived for twelve replicate measurements of each standard concentration. Taking a 10% coefficient of variation (CV) as the upper limit of imprecision, the working range of the assay is 1 to 500 IU hCG/L serum. However, as the profile shows (FIG. 4), the CV in the linear range of the assay is better than 5%.

As shown in FIG. 4, the fluorescence intensity, after reaching a relatively prolonged plateau, begins to decline with increasing hCG concentration. This is presumably due to the high dose hook effect which is often observed with sandwich assays.

Precision

To evaluate the precision of the assay, three levels of human serum controls for immunoassay (Bio-Rad) and a pooled human serum sample were used. Within-run precision was determined by analyzing 21 replicates of each sample in the same run. Assessment of between-run precision was by repeat analysis, in duplicate, of the control samples in five successive runs. The day-to-day precision was estimated by determining, in duplicate, the hCG concentration of the same samples on 12 different occasions during a 30 day period (Table 1).

Dilution Linearity

Linearity was assessed by serial dilution of three different patient samples with the zero standard serum. Assaying for hCG, the concentration in the undiluted samples were used to calculate the expected values of the diluted samples. As shown in Table 3, there was a linear relationship between the expected and measured hCG values, with excellent correlation between them.

Analytical Recovery

To determine the analytical recovery of the assay, hCG at three different concentrations was added to three serum pools. Assays were performed on each sample before and after the addition. Measured and recovered concentrations are shown in Table 4. Recovery ranged from 92 to 105%, with an average value of 101.5%.

Cross-reactivity

Interference from other hormones was tested by two experiments. In one, the response of the assay to increasing concentrations of hTSH, hFSH and hLH in the absence of hCG was measured. Of the concentrations of hTSH (50-200 mIU/L), and hFSH (50-200 IU/L) tested, none produced a response significantly different than the two SD range of the hCG negative sample. The hCG response of the sample was significantly increased with hLH at concentrations greater than 100 IU/L with a maximum cross-reactivity of about 18% (Table 5).

In the second experiment, the same concentrations of these hormones were added to serum samples containing a fixed concentration of hCG (100 IU/L). This was done to evaluate the possibility that at high concentrations, these hormones might compete with hCG for binding to the biotinylated anti-hCG-alpha monoclonal antibody, thus producing a false negative effect. With high concentrations of hTSH and hFSH present, the hCG response did not change more than the two SD range of the expected value (i.e. 100 IU/L). Similarly, hLH did not appear to have any false negative effect on hCG detection, but rather generated a false positive interference. The degree of cross-reaction was the same as that noted in the previous experiment, cross-reacting at a maximum of about 17%.

Because of the significant contribution of hLH to the assay response at a concentration range that corresponds to physiological as well as pathological levels (about 200-400 IU hLH/L), the possibility of including a scavenger anti-hLH antibody to the system was investigated. A monoclonal antibody against the beta subunit of hLH appeared most effective. This antibody at a concentration of 1 µg/mL (i.e. 50 ng/well) was capable of practically eliminating the hLH cross-reaction (Table 5). Only about 2% cross-reactivity remained at 500 IU/L, indicating that hLH, even at pathological concentrations, would not lead to any false positive or negative results in the hCG assay.

Figure 5:
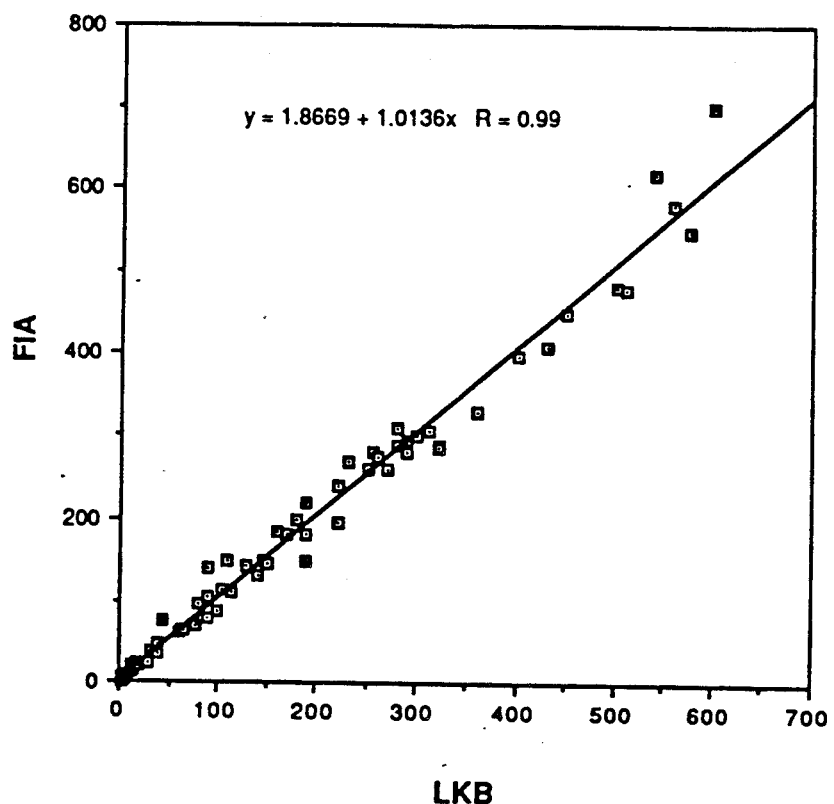
FIG. 5 shows a correlation between an assay in accordance with the invention and a shown assay (LKB) on 74 patient samples measured in duplicate.
Figure 6:
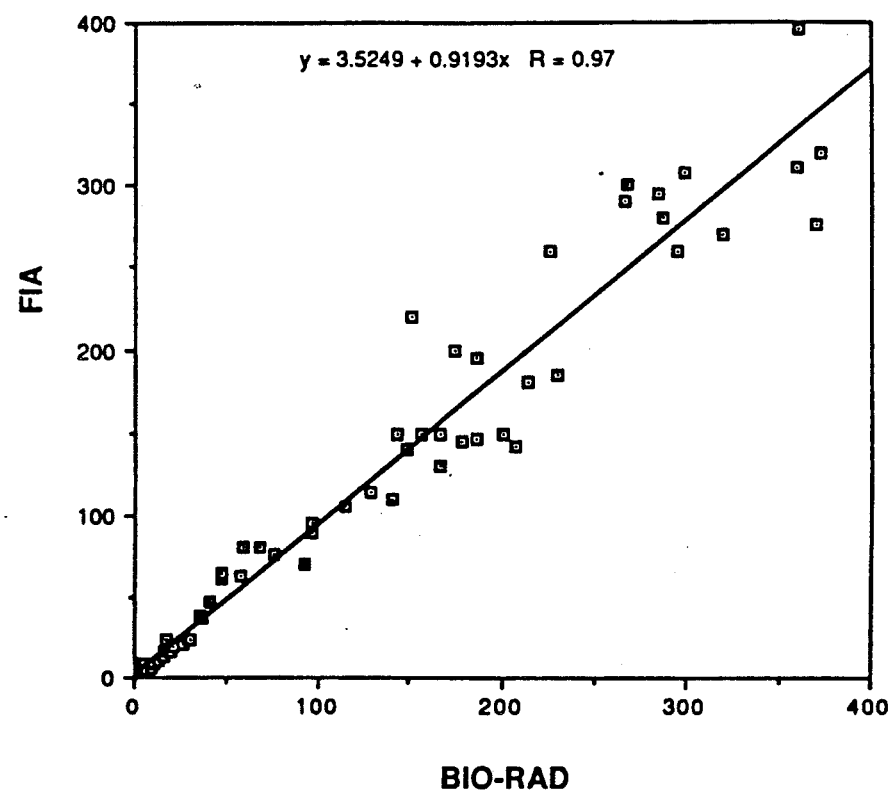
FIG. 6 shows a correlation between an assay method in accordance with the invention and a known assay method (Bio-Rad) on 64 patient samples measured in duplicate.

Correlation with Immunoradiometric and Immunofluorometric Assays hCG concentrations in serum samples from pregnant and non-pregnant females were assayed, in duplicate, by the present method (TRFIA) and the comparative immunoradiometric (Bio-Rad) and immunofluorometric (LKB) procedures. There was a good agreement between the values obtained with the test method and the comparative kits. The correlation coefficients with the LKB and Bio-Rad assays were R=0.99 and R=0.97 respectively, indicating the reliability of the present procedure (FIGS. 5 and 6).

TABLE 2

WITHIN-RUN, BETWEEN-RUN, AND DAY-TO-DAY PRECISION OF THE ASSAY

| Within-Run (n = 21) hCG IU/L | | | Between-Run (n = 16) hCG, IU/L | | | Day-to-Day (n = 12) hCG;IU/L | | |
|---|---|---|---|---|---|---|---|---|
| Mean | SD | %/CV | Mean | SD | %/CV | Mean | SD | %/CV |
| 14.5 | 0.62 | 4.33 | 14.52 | 0.90 | 6.2 | 13.45 | 1.30 | 9.7 |
| 52 | 2.74 | 5.26 | 57.06 | 3.41 | 5.9 | 54.09 | 2.80 | 5.2 |
| 210 | 9.03 | 4.3 | 225.6 | 18.2 | 8.0 | 212.2 | 15.3 | 7.2 |
| 400 | 24.3 | 6.08 | — | — | — | 454.4 | 31.5 | 6.9 |

TABLE 3

RESULTS OF DILUTION OF SERA WITH HIGH hCG CONCENTRATION

| Dilution | Sample 1[a] Expected | Sample 1[a] Measured | Sample 2[b] Expected | Sample 2[b] Measured | Sample 3[c] Expected | Sample 3[c] Measured |
|---|---|---|---|---|---|---|
| None | — | 440 | — | 450 | — | 310 |
| ½ | 220 | 210 | 225 | 220 | 155 | 160 |
| ¼ | 110 | 100 | 112 | 105 | 78 | 79 |
| ⅛ | 55 | 49 | 56 | 52 | 39 | 40 |
| 1/16 | 28 | 25 | 28 | 26 | 19 | 21 |
| 1/32 | 14 | 13 | 14 | 14 | 10 | 10 |

[a], R = 1.00, Slope = 0.9567, y = −2.1464
[b], R = 1.00, Slope = 0.9778, y = −1.9091
[c], R = 1.00, Slope 1.0281, y = 0.2552

TABLE 4

RECOVERY OF hCG ADDED TO THREE SERUM POOLS[a]

| hCG added | Measured | hCG, IU/l Recovered | % Recovery[b] |
|---|---|---|---|
| Sample 1 | | | |
| 0.0 | 1.7 | — | — |
| 49.5 | 47 | 45.3 | 92 |
| 99 | 105 | 103.3 | 104 |
| 198 | 210 | 203.3 | 105 |
| Sample 2 | | | |
| 0.0 | 17 | — | — |
| 49.5 | 67 | 50 | 101 |
| 99 | 118 | 101 | 102 |
| 198 | 215 | 198 | 100 |
| Sample 3 | | | |
| 0.0 | 98 | — | — |
| 49.5 | 150 | 52 | 105 |
| 99 | 200 | 102 | 103 |
| 198 | 300 | 202 | 102 |

[a], 300 μL aliquots of each standard hCG preparation was added to 3 ml aliquots of each serum pool.
[b], % Recovery = (Concentration recovered/Concentration added)

added to 3 ml aliquots of each serum pool. b, % Recovery =(Concentration recovered/Concentration added)

TABLE 5

CROSS-REACTIVITY WITH hLH

| | hCG Equivalent | % Crossreaction | hCG Equivalent | % Crossreaction |
|---|---|---|---|---|
| LH added[a] | | | | |
| 100 | 12 | 12 | 15 | 15 |
| 200 | 30 | 15 | 32 | 16 |
| 500 | 90 | 18 | 86 | 17 |
| LH added[b] | | | | |
| 100 | 1.0 | 1.0 | 0.0 | 0.0 |
| 200 | 1.7 | 0.8 | 0.0 | 0.0 |
| 500 | 14 | 2.8 | 5.0 | 1.0 |

[a], in the absence of anti-hLH
[b], in the presence of anti-hLH

EXAMPLE 4

Labelling of Monoclonal Antibodies

Generally, selected monoclonal antibodies may be directly labelled with BCPDA. For example, a monoclonal antibody specific to cortisol can be labelled as follows. 0.20 mg/ml of the monoclonal antibody in 0.1 M carbonate buffer of pH 9.1 was mixed with a freshly prepared absolute ethanolic solution of BCPDA by adding the solution in 4 aliquots at 1 minute intervals while continually vortexing the solution. The excess of BCPDA added over the amino group concentration on the monoclonal was 0.5 fold. The working monoclonal antibody solution had a concentration of 2 μg/ml. The diluent for the working solution was 50 mM Tris buffer of pH 7.80 containing 9 g NaCl, 10 g BSA and 0.5 g sodium azide per liter.

Preparation of Thyroglobulin-Cortisol Conjugate

A standard procedure to prepare conjugates as described in Erlanger et al (1959) "Steroid-Protein Conjugates: Preparation and Characterization of Conjugates of BSA with Progesterone, Deoxycorticosterone and Esterone" *J. Biol. Chem.* 234, 1090 was modified as described by Elder et al (1987) "An EnzymeLinked-/Immunosorbent Assay (ELISA) for Plasma Progesterone: Immobilized Antigen Approach" *Clin. Chem. Acta.* 162, 199 to prepare the desired conjugate. In accordance with the modified method, cortisol 21hemisuccinate was used instead of progesterone-3-o-carboxymethyloxime.

Coating of Microtitration Strips

The coating buffer was a 0.1 M carbonate solution of pH 9.5. The blocking buffer was a 50 mM sodium phosphate solution of pH 7.4 containing 9 NaCl, 1 g gelatin and 1 mL polyoxyethylenesorbitan monolaurate (Tween 20) per liter. The wash solution was a 9 g/L NaCl solution containing 0.5 mL Tween 20 and 0.5 g sodium azide per liter.

The strips were coated overnight at room temperature with 100 μL of a 6 μg/mL solution of cortisol-thyroglobulin conjugate in the coating buffer. After coating, the strips were rinsed once with the wash solution, blocked for 1 h at room temperature with 200 μL of the blocking buffer, washed twice and dried overnight at room temperature, preferably under reduced pressure. Stored in sealed plastic bags at 4° C. with desiccant, they are stable for several weeks.

Monoclonal Antibody Cortisol Assay Procedure

Before initiating the assay, the cortisolthyroglobulin coated strips were washed twice with the wash solution. Twenty μL of standards were pipetted into each well and 100 μL of the BCPDA-labelled monoclonal antibody working solution containing $10^{-5}$ M EuCl$_3$ was added. The strips are then briefly shaken and incubated for 1 h at 37° C. The strips are washed three times with the wash solution and dried with a stream of air. Surface fluorescence of the complex, thyroglobulin-cortisol-antibody-BCPDA-Eu$^{3+}$ was measured on the CyberFluor 615 Immunoanalyzer.

Figure 8:
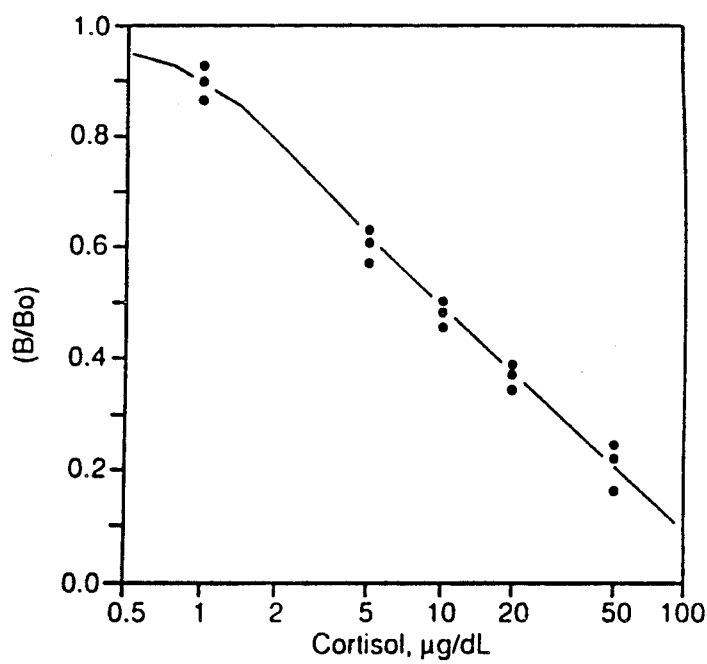
FIG. 8 is a curve generated by TRFIA for a competition assay directly labelled cortisol antibodies.

The monoclonal anti-cortisol antibody that was labelled at the optimal molar ratio of 18 BCPDA per protein molecule was used to generate a standard curve for a competition type assay using aqueous cortisol standards as show in FIG. 8.

EXAMPLE 5

A second polyclonal antibody specific to the monoclonal antibody of Example 4 may be used to analyze for the presence of the analyte-cortisol. The polyclonal antibody, which is specific to the monoclonal, may be a polyclonal affinity purified goat anti-mouse IgG. The polyclonal is labelled as per the method of Example 4. The working solution of the polyclonal antibody is at a concentration of 20 µg/ml.

The thyroglobulin-cortisol conjugate and microtitration strips of Example 4 were used.

The polyclonal antibody assay procedure of Example 4 was followed where the monoclonal antibody as labelled was used in the first step. After incubation and washing, 100 µL of the working (20 µg/ml) labelled polyclonal; i.e. second antibody solution containing $10^{-5}$ M EuCl$_3$ was added and incubated for 30 min at 37° C. The wells were then washed and the assay completed by proceeding as above. In this case, the fluorescent complex on the dry solid-phase is thyroglobulin-cortisol-antibody-second antibody-BCPDA-Eu$^{3+}$.

This competition assay system produced a calibration curve similar to that of FIG. 8 thereby indicating the utility of this system as a viable form of immunoassay.

EXAMPLE 6

As with Examples 4 and 5, it is possible to directly label other monoclonal antibodies The α-fetoprotein (AFP) monoclonal antibody may be labelled with BCPDA as per the method of Example 4. AFP standards were pipetted into AFP antibody coated microtitration wells. 100 µL of the directly labelled antibody solution (5 µg/ml in antibody containing $10^{-5}$ M Eu$^{3+}$) were added and incubated for 90 min at 37° C. The wells were washed three times with the wash solution, dried for 3 min with cool air and the fluorescence of the labelled monoclonal was measured on the CyberFluor Model 615 (trade mark) Immunoanalyzer The solid phase sandwich type assay demonstrated the utility of the labelled monoclonal antibody By loading a variety of concentrations of AFP into the wells, a calibration curve of fluorescent intensity vs. concentration of AFP can be developed.

In the above Examples, the preferred lanthanide metal ion used in the fluorescent chelate is europium. It is appreciated that other lanthanide metal ions are usable, such as, terbium, gadolinium, samarium and dysprosium.

Although preferred embodiments of the invention have been described herein in detail, it will be understood by those skilled in the art that variations may be made thereto without departing from the spirit of the invention or the scope of the appended claims.

The embodiments of the invention in which an exclusive property or privilege is claimed are defined as follows:

1. An immunoassay method to determine the quantity of immunoreactive substances immobilized on a solid phase comprising:
   a) reacting immobilized immunoreactive substances with complementary immunoreactive substances to which are connected moieties of a ligand forming with lanthanide metal ion a fluorescent chelate label wherein the metal ion is stably retained by said ligand, said complementary immunoreactive substances being in amount effective for binding with said immobilized immunoreactive substances, said ligand being a moiety of a 4,7-diphenyl-1,10-phenathroline-2,9-dicarboxylic acid capable of fluorescing in the presence of said lanthanide metal ion,
   b) removing an excess complementary immunoreactive substances which are not bound to said immobilized substances by washing said solid phase with a washing solution, said fluorescent chelate label stably retaining said lanthanide metal ion with said ligand during said washing of said solid phase, said chelate label being capable of fluorescing after said washing,
   c) measuring the fluorescence of the chelate label on bound complementary immunoreactive substances in the presence of said metal ion which is stably retained with said chelate, and
   d) obtaining a value indicative of the quantity of said complementary immunoreactive substances bound to said immobilized immunoreactive substances.

2. A method according to claim 1 in which the chelate is at least air dried before its fluorescence is measured.

3. A method of claim 1 in which the immunoreactive substance immobilized on said solid phase is selected from the group consisting of cortisol, cortisol amine, thyroxine, digoxin, biotin, α-fetoprotein, human chorionic gonadotropin, ferritin, thyrotropin, follitropin, lutropin, thyroxine, binding globulin, growth hormone, prolactin, antibody to cortisol, antibody to α-fetoprotein, antibody to human chorionic gonadotropin and antibody to Rubella virus.

4. A method of claim 1 in which said lanthanide metal ion is selected from the group consisting of europium, terbium, gadolinium, samarium and dysprosium.

5. A method of claim 3 in which said immobilized immunoreactive substance is α-fetoprotein, said complementary immunoreactive substances are monoclonal antibodies specific to said α-fetoprotein, said monoclonal antibodies having directly connected thereto said fluorescent chelate labels.

6. A method of claim 3 in which said immobilized immunoreactive substances are cortisol molecules, said complementary immunoreactive substances are monoclonal antibodies specific to said cortisol, said monoclonal antibodies having directly connected thereto said fluorescent chelate labels.

7. A method of claim 3 in which said immobilized immunoreactive substances are cortisol molecules, said complementary immunoreactive substances are antibodies specific to said cortisol molecules, said antibodies being linked by a linking bifunctional reagent to a protein labelled with said fluorescent chelate labels.

8. A method of claim 7 in which said protein is bovine serum albumin and said linking reagent is sulfosuccinimidyl4-(N-maleimidomethyl)cyclohexane-1-carboxylate or derivatives thereof.

9. A method of claim 3 wherein said immobilized immunoreactive substances are monoclonal antibodies specific to cortisol which is bound to said solid phase, said complementary immunoreactive substances are polyclonal antibodies specific to said monoclonal antibodies, said polyclonal antibodies having directly connected thereto said fluorescent chelate labels 10. A method of claim 3, wherein said immobilized immunoreactive substances are selected from the group consisting of human chorionic gonadotropin and α-fetoprotein, said complementary immunoreactive substances are antibodies specific to the selected immobilized immunoreactive substances, said antibodies being biotinylated and having bound thereto avidin or streptavidin wherein advidin or streptavidin has connected directly thereto said fluorescent chelate labels.

11. A method of claim 1 in which said complementary immunoreactive substances comprise a two component system, a first component is immunoreactive with said immobilized immunoreactive substance, said first component being biotinylated and being in an amount effective for binding with said immobilized immunoreactive substances, any excess of said first component being removed, reacting a second component of avidin or streptavidin with said biotinylated first component, said second component being in an amount effective for binding with said first component and being labelled with moieties of a ligand forming with lanthanide metal ion a fluorescent chelate label.

* * * * *